(12) United States Patent
Roberts et al.

(10) Patent No.: US 7,091,236 B1
(45) Date of Patent: Aug. 15, 2006

(54) METHOD FOR INCREASING THE BIOAVAILABILITY OF GLYCOPYRROLATE

(75) Inventors: Alan Roberts, Woodstock, GA (US); Bala Venkataraman, Alpharetta, GA (US)

(73) Assignee: Sciele Pharma, Inc., Atlanta, GA (US)

( * ) Notice: Subject to any disclaimer, the term of this patent is extended or adjusted under 35 U.S.C. 154(b) by 248 days.

(21) Appl. No.: 10/644,530

(22) Filed: Aug. 20, 2003

(51) Int. Cl.
*A61K 31/40* (2006.01)

(52) U.S. Cl. .................................... 514/424

(58) Field of Classification Search .................. None
See application file for complete search history.

(56) References Cited

U.S. PATENT DOCUMENTS

| | | | |
|---|---|---|---|
| 6,407,128 B1 | 6/2002 | Scaife et al. | |
| 6,455,557 B1 | 9/2002 | Pellegrini et al. | |

FOREIGN PATENT DOCUMENTS

WO    WO 01/08681 A1    2/2001

OTHER PUBLICATIONS

Ali-Melkkila er al, "Glycopyrrolate: pharmacokinetics and some pharmacodynamic findings,"*Acta Anaesthesiol. Scand.*, 33: 513-517 (1989).
Ali-Melkkila et al., "Pharmacokinetics and related pharmacodynamics of anticholinergic drugs,"*Acta Anasthesiol. Scand.*, 37: 633-642 (1993).
Chen, "Troglitazone: An antidiabetic agent," *Am J. of Health-Syst. Pharm.*, 55:905-925 (1998).
Evans, "Influence of Dietary Components on the Gastrointestinal Metabolism and Transport of Drugs," *Therapeutic Drug Monitoring*, 22: 131-136 (2000).
Greene et al., "Clinical Pharmacokinetics of Nefazodone," *Clin. Pharmacokinet.*, 33(4): 260-275 (1997).
Gillen et al., "Problems related to acid rebound and tachyphylaxis," *Best Pract. & Res. Clin. Gastroenterology*, 15(3): 487-495 (2001).
Kirk, "Significant Drug-Nutrient Interactions,"*Amer. Fam. Phys.*, 51(5): 1175-1182 (1995).
Loi et al., "Clinical Pharmacokinetics of Troglitazaone,"*Clin. Pharmacokinet.*, 37(2):91-104 (1999).
Martinez et al., "A Mechanistic Approach to Understanding the Factors Affecting Drug Absorption: A Review of Fundamentals,"*J. Clin. Pharmacol.*, 42: 620-643 (2002).
Pelkonen et al., "In vitro prediction of gastrointestinal absorption and bioavailability: and experts' meeting report,"*Eur. J. Clin. Pharmacol.*, 57: 621-629 (2001).
Rautakorpi et al., "Pharmacokinetics and Oral Bioavailability of Glycopryrrolate in Children,"*Pharmacology & Toxicology*, 83: 132-134 (1998).
Rautakorpi et al., "Pharmacokinetics of Glycopyrrolate in Children,"*J. Clin. Anesth.*, 6: 217-220 (1994).
Singh, "Effects of Food on Clinical Pharmacokinetics,"*Clin. Pharmacokinet.*, 37(3): 213-255 (1999).
Temple et al., "Rifapentine: Its Role in the Treatment of Tuberculosis,"*The Annals of Pharmacotherapy*, 33: 1203-1210 (1999).
Toothaker et al., "The Effect of Food on Drug Bioavailability," *Ann. Rev. Pharmacol. Toxical.*, 20: 173-199 (1980).
van Leerdam et al. "The role of acid suppressants in upper gastrointestinal ulcer bleeding", *Best Pract.&Res. Clin. Gastroenterology*, 15(3): 463-475 (2001).
Walter-Sack et al., "Influence of Diet and Nutritional Status on Drug Metabolism,"*Clin. Pharmacokinet.*, 31(1): 47-64 (1996).
Welling, "Interactions Affecting Drug Absorption," *Clin. Pharmacokinet.*, 9: 404-434 (1984).

*Primary Examiner*—Phyllis G. Spivack
(74) *Attorney, Agent, or Firm*—Leydig, Voit & Mayer, Ltd.

(57) ABSTRACT

The invention relates to a method of increasing the bioavailability of glycopyrrolate by administration of a therapeutically effective amount of glycopyrrolate without food.

5 Claims, 2 Drawing Sheets

Mean Plasma Glycopyrrolate Concentration versus Time

Mean Plasma Glycopyrrolate Concentration versus Time (Semi-log)

METHOD FOR INCREASING THE BIOAVAILABILITY OF GLYCOPYRROLATE

FIELD OF THE INVENTION

The invention relates to methods for increasing the bioavailability of drug products containing glycopyrrolate.

BACKGROUND OF THE INVENTION

Glycopyrrolate, the active pharmaceutical ingredient in Robinul® tablets, Robinul® Forte tablets and Robinul® injection, is a quaternary ammonium compound having the chemical name 3-[(cyclopentylhydroxyphenylacetyl)oxy]-1,1-dimethylpyrrolidinium bromide. Glycopyrrolate is an anticholinergic and antispasmodic that inhibits gastrointestinal nerve receptor sites that stimulate both the secretion of stomach acid and smooth muscle activity in the digestive tract. Accordingly, it diminishes the volume and free acidity of gastric secretions and controls excessive pharyngeal, tracheal, and bronchial secretions.

Glycopyrrolate is indicated for use as adjunctive therapy in the treatment of peptic ulcer. See PHYSICIANS' DESK REFERENCE (57th ed., Medical Economics Co., 2003). The most frequent adverse reactions to glycopyrrolate include those that are common to anticholinergics generally including, for example, xerostomia, decreased sweating, urinary hesitancy and retention, blurred vision, tachycardia, palpitations, headaches, dizziness, nausea, vomiting, nervousness, and other reactions.

Pharmacokinetic studies have not previously been conducted to evaluate the effect of food on the pharmacokinetics of glycopyrrolate. It is desirable to increase the oral bioavailability of a drug substance, such as glycopyrrolate, to increase the extent of the therapeutic effect on the user. In general, food has a variable effect on the bioavailability of an active agent. Drug-food interactions may result in reduced, delayed or increased systemic drug availability. See, e.g., Clin Pharmacokinet 1984 Sep–Oct; 9(5):404–34. Food may interact with a coadministered drug at the following phases: (i) before and during gastrointestinal absorption; (ii) during distribution; (iii) during metabolism; and (iv) during elimination. See Clin Pharmacokinet 1999 September; 37(2):213–55. For some drugs such as, for example, nefazodone and troglitazone, bioavailability increases with food. See Clin Pharmacokinet 1997 October; 33(4):260–75; Clin Pharmacokinet 1999 August; 37(2):91–104.

There remains a need for a method of treatment of peptic ulcer and other gastrointestinal disorders using glycopyrrolate that has increased oral bioavailability and, thus, improved efficacy following administration to human patients.

BRIEF SUMMARY OF THE INVENTION

Figure 1:
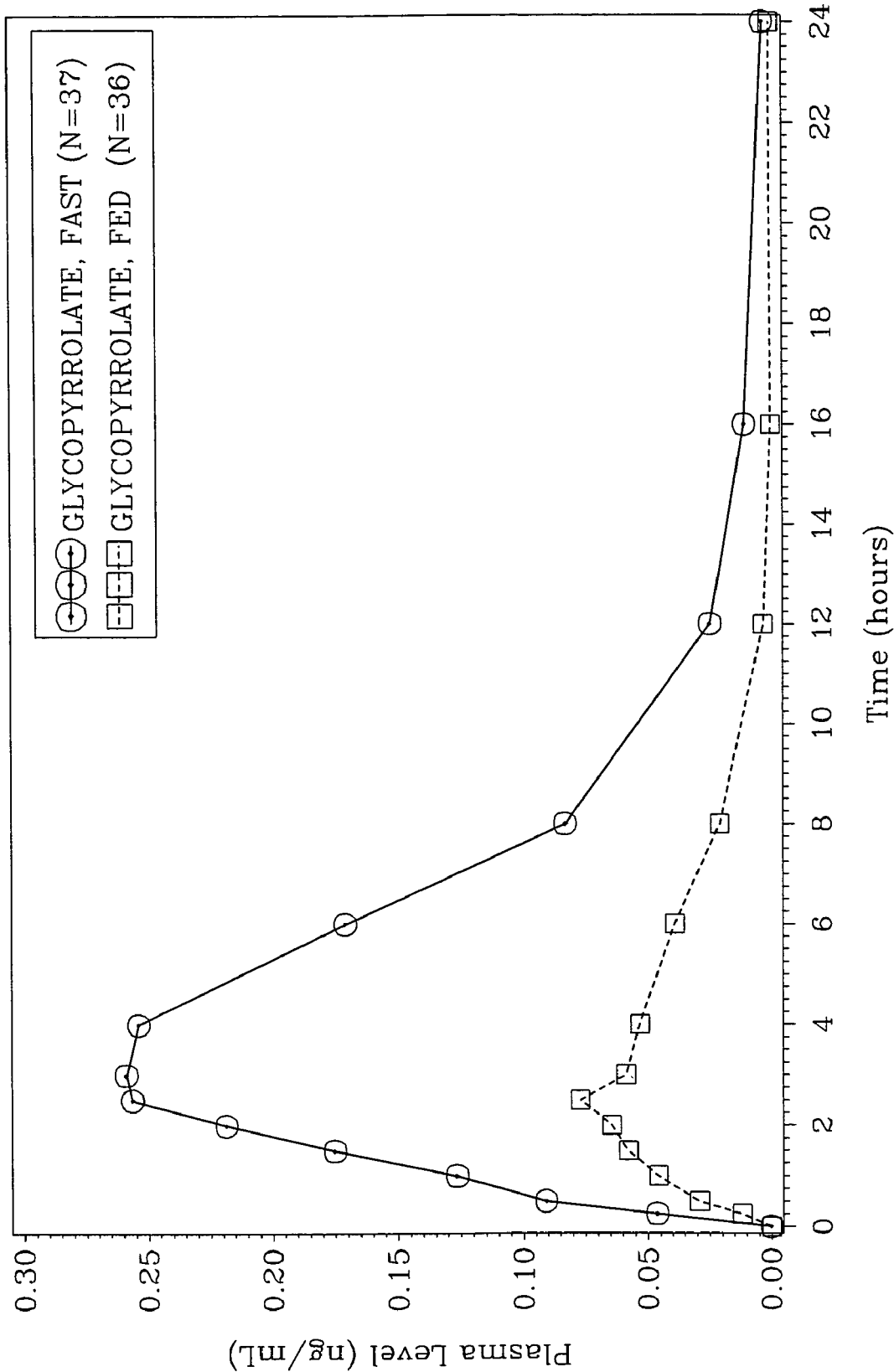
FIG. 1 is a plot of the mean plasma concentration of glycopyrrolate in nanograms per milliliter versus the time elapsed from administration of a liquid glycopyrrolate dosage form (2 mg dose of 1 mg/5 mL liquid solution). Two plots are shown for the liquid glycopyrrolate dosage form administered under fasted and fed conditions.

The subject of this invention is the unexpected finding that administration of glycopyrrolate under fasted conditions (i.e., without food), increases the extent of absorption via the oral dosage form in human subjects.

One aspect of this invention is a method of increasing the bioavailability of glycopyrrolate in a human patient receiving glycopyrrolate therapy wherein the glycopyrrolate is contained in a pharmaceutical composition, which method comprises administering a therapeutically effective amount of glycopyrrolate to the patient without food.

Another aspect of the invention is providing a method of increasing the extent of glycopyrrolate absorption as measured by the drug concentration attained in the blood stream over time of a patient receiving the drug in an oral dosage form which method comprises administering a therapeutically effective amount of glycopyrrolate to the patient without food.

The invention further includes a method of increasing the oral bioavailability of glycopyrrolate to a patient receiving glycopyrrolate therapy comprising administering to the patient a pharmaceutical tablet comprising about 1 mg to about 10 mg of glycopyrrolate under fasted conditions, wherein the administration results in an increase of the maximum plasma concentration ($C_{max}$) and the extent of absorption of glycopyrrolate at t=24 hours ($AUC_{0-24\ hrs}$) as compared to the administration of glycopyrrolate under fed conditions.

The invention is also directed to a method for treating peptic ulcer or other gastrointestinal disorders in a patient, which comprises administering a therapeutically effective amount of glycopyrrolate without food. To this end, a patient is administered glycopyrrolate, wherein the resulting maximum plasma concentration ($C_{max}$) after administration is at least about 2.5 ng/mL.

The invention further relates to a kit comprising a pharmaceutical composition comprising a therapeutically effective amount of glycopyrrolate and a pharmaceutically acceptable carrier, prescribing information, and a container. The prescribing information includes advice to a patient regarding the administration of glycopyrrolate without food to improve bioavailability.

DETAILED DESCRIPTION OF THE INVENTION

The present invention is directed to methods and compositions for the treatment of certain gastrointestinal conditions. These conditions include, but are not limited to, peptic ulcer, duodenal ulcer, dyspepsia (indigestion), gastroesophageal reflux disease (GERD), irritable bowel syndrome (IBS), acid-related diseases of the gastrointestinal tract, bleeding of the stomach and duodenum, esophagitis (inflammation of the esophagus), and gastritis.

In addition to the treatment of gastrointestinal conditions, the methods and compositions of the present invention are useful in the treatment of a variety of conditions or pathologies having mild to severe symptoms that can limit a patient's lifestyle as well as limit a patient's ability to interact and communicate with others. Such conditions and pathologies include, but are not limited to, gustatory sweating, Frey's syndrome, sialhorrhea (excessive drooling), hyperhidrosis, Meniere's disease and myasthenia gravis.

It has been discovered that glycopyrrolate can be administered to human patients in a regime that increases the therapeutic effectiveness of glycopyrrolate such patients.

Specifically, when administered under fasted conditions, glycopyrrolate exhibits increased oral bioavailability in patients.

Therefore, according to one aspect, the present invention provides a method of increasing the oral bioavailability of glycopyrrolate in a human patient comprising administering to the patient a therapeutically effective amount of glycopyrrolate under fasted conditions.

As used herein, the term "bioavailability" generally means the rate and extent to which the active ingredient is absorbed from a drug product and becomes available at the site of action. See Code of Federal Regulations, Title 21, Part 320.1 (2003 ed.). For oral dosage forms, bioavailability relates to the processes by which the active ingredient is released from the oral dosage form and moves to the site of action. Bioavailability data for a particular formulation provides an estimate of the fraction of the administered dose, for example, an oral tablet, that is absorbed into the systemic circulation.

As used herein, the terms "without food," "fasted conditions," and "empty stomach" are defined to mean, in general, the condition of not having consumed food during the period between from at least about 30 minutes prior to the administration of glycopyrrolate to at least about 1 hour after the administration of glycopyrrolate.

In contrast, the term "with food" is defined to mean, in general, the condition of having consumed food during the period between from about 1 hour prior to the administration of glycopyrrolate to about 2 hours after the administration of glycopyrrolate. Preferably, the food is a solid food with sufficient bulk and fat content that it is not rapidly dissolved and absorbed in the stomach. More preferably, the food is a meal, such as breakfast, lunch or dinner.

Advantageously, glycopyrrolate administered any time of day without food. Preferably, food is not consumed during the period between from at least about 30 minutes prior to the administration of glycopyrrolate to at least about 1 hour after the administration of glycopyrrolate.

Glycopyrrolate is preferably administered in the morning under fasted conditions. Any suitable administration time in the morning may be utilized, for example, around 8:00 a.m. More preferably, glycopyrrolate is administered in the morning without food with the patient having fasted for at least about 10 hours. For example, glycopyrrolate is administered at around 8:00 a.m. with the patient having fasted since around 10:00 p.m. the night before.

The methods of the present invention are directed to the administration of a therapeutically acceptable amount of glycopyrrolate or pharmaceutically acceptable salt or prodrug of glycopyrrolate. The present invention further contemplates the use glycopyrronium bromide and of other forms of glycopyrronium associated with other ionic components, such as other salts of glycopyrronium.

Glycopyrrolate exists in four distinct stereoisometric forms due to the presence of two chiral centers in the glycopyrrolate molecule. One of the two enantiomeric pairs of diastereomers of glycopyrrolate is (R,R)-glycopyrrolate and (S,S)-glycopyrrolate, and the other enantiomeric pair is (R,S)-glycopyrrolate and (S,R)-glycopyrrolate. The glycopyrrolate suitable for use in the present invention may be a mixture of two or more of the four stereoisomers. Alternatively, glycopyrrolate may be used in the form of one isolated enantiomer.

Enantiomerically enriched glycopyrrolate may also be used. Enantiomerically enriched (S,S)-glycopyrrolate, (R,R)-glycopyrrolate, (S,R)-glycopyrrolate, and (R,S)-glycopyrrolate, and methods of their preparation, are described in U.S. Pat. Nos. 6,063,808, 6,204,285, PCT Application WO 98/00109, and PCT Application WO 98/00132, all incorporated herein by reference.

In general, a suitable dose of a therapeutically effective amount of glycopyrrolate or a pharmaceutically acceptable salt thereof for administration to a patient will be between approximately 0.0005 to 300 mg per kilogram body weight of the recipient per day, preferably between approximately 0.0005 and 50 mg/kg/day, and most preferably between approximately 0.001 to 10 mg/kg/day. A typical dose of a therapeutically effective amount of glycopyrrolate or pharmaceutically acceptable salt thereof in human patients is about 1–100 mg/day, preferably about 2–50 mg/day, and more preferably about 3–10 mg/day.

If desired, the effective daily dose of glycopyrrolate may be administered as two, three, four, five, six or more sub-doses administered separately at appropriate intervals throughout the day, optionally, in unit dosage forms. The typical amount of glycopyrrolate in a unit dosage form useful in the present invention is about 1–10 mg, preferably about 1–5 mg, and most preferably about 1–2 mg. Each such sub-dose contains a therapeutically effective amount of glycopyrrolate.

In accordance with the inventive method, glycopyrrolate may be administered without food at multiple times per day or, alternatively, once per day. When administered at multiple times throughout the day, each individual dose contains a therapeutically effective amount of glycopyrrolate.

A preferred dosing of a therapeutically effective amount of glycopyrrolate is one milligram three times daily, for example, in the morning, early afternoon, and at bedtime. The bedtime dose may optionally be two milligrams to assure overnight control of symptoms. After the initial dosage of glycopyrrolate, an adequate dosage for maintenance of one milligram twice per day is often suitable. Alternatively, glycopyrrolate may be administered two or three times daily with two milligrams per dose. Preferably, with all glycopyrrolate dosing schedules, the time periods between administrations are equal.

The components of the combination which may be referred to as active ingredients may be administered for therapy to an animal (e.g., a mammal), including a human, in any conventional manner. While it is possible for the active ingredients of the combination to be administered as the raw chemical, it is preferable to present them as a pharmaceutical formulation. Pharmaceutical formulations according to the present invention comprise the active ingredients (that is, the combination of glycopyrrolate or a pharmaceutically acceptable salt thereof and one or more acid suppressant agents) together with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the combination are administered separately, they are generally each presented as a pharmaceutical formulation.

The combinations of the invention can also include other medicinal agents, pharmaceutical agents, carriers, adjuvant diluents and other pharmaceutical preparations known to those skilled in the art. Those agents are known to those skilled in the art and are generally described as being biologically inactive and can be administered to patients without causing deleterious interactions with the active agents. For example, glycopyrrolate may be combined with other active agents for the treatment of gastrointestinal disorders or comorbid diseases associated with gastrointestinal condition including adjunct therapy for the treatment of peptic ulcers. Suitable acid suppressants include H$_2$-receptor antagonists (e.g., cimetidine, famotidine, nizatidine, ranitidine) or proton pump inhibitors (e.g., omeprazole, esomeprazole, lansoprazole, pantoprazole, rabeprazole).

Examples of carriers or excipients for oral administration include cornstarch, lactose, magnesium stearate, microcrystalline cellulose and stearic acid, povidone, dibasic calcium phosphate and sodium starch glycolate. Any carrier suitable for the desired administration route is contemplated by the present invention.

Suitable formulations include those suitable for oral, rectal, nasal, topical (including transdermal, buccal and sublingual), vaginal or parenteral (including subcutaneous, intramuscular, intravenous, intraarterial, intraperitoneal, intraspinal, and intradermal) administration. Suitable glycopyrrolate formulations useful in the present invention are described in WO 01/08681, incorporated herein by reference.

The formulations may be prepared by any methods well known in the art of pharmacy, for example, using methods such as those described in Gennaro et al., Remington's Pharmaceutical Sciences (18th ed., Mack Publishing Co., 1990), especially Part 8: Pharmaceutical Preparations and their Manufacture. Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents, and wetting agents.

The combinations of the invention can provide controlled, slow release, or sustained release of the therapeutic compounds over a predetermined period of time. Administration of the combination using these formulations allows for a desired concentration of the compound to be maintained in the bloodstream of the patient for a longer period of time that with conventional formulations. Slow release, controlled, or sustained release formulations are known to those skilled in the art and include formulations such as coated tablets, pellets, capsules, dispersion of the active agents in a medium that is insoluble in physiologic fluids, or where the release of the active agents follows degradation of the formulation due to mechanical, chemical, or enzymatic activity.

Preferred methods of administration include oral routes. The compositions of the present invention can be contained in a pill, capsule, or tablet, each containing a predetermined amount of active ingredient and preferably coated for ease of swallowing; as a powder or granules; or as a solution or suspension. For oral administration, fine powders or granules may contain diluting, dispersing, and or surface active agents and may be present in a solution or suspension in water or syrup, capsules or sachets in the dry state, in a nonaqueous solution or suspension wherein suspending agents may be included, or in tablets wherein binders and lubricants may be included. Components may be added such as flavoring, preserving, suspending, thickening or emulsifying agents. Such preparations are known or apparent to those skilled in the art.

Oral delivery methods are often limited by chemical and physical barriers imposed by the body, such as the varying pH in the gastrointestinal tract, exposure to enzymes, and the impermeability of the gastrointestinal membranes. Methods of the present invention for orally administering the combination may also include the co-administration of adjuvants with the compositions of the present invention. For example, nonionic surfactants such as polyoxyethylene oleyl ether and n-hexadecyl polyethylene ether can be administered with or incorporated into the combinations of the present invention to artificially increase the permeability of the intestinal walls. Other methods include the co-administration of enzymatic inhibitors with the combinations of the present invention. The active ingredients may also be present as a bolus or paste or may be contained within liposomes and emulsions.

Formulations for rectal administration may be presented as a suppository or enema.

For parenteral administration, suitable formulations include aqueous and non-aqueous sterile injection. The formulations may be presented in unit-dose or multi-dose containers, for example, sealed vials and ampoules, and may be stored in a freeze dried (lyophilized) condition requiring only the addition of the sterile liquid carrier, for example, water, prior to use.

Formulations suitable for administration by nasal inhalation include fine dusts or mists which may be generated by means of metered dose pressurized aerosols, nebulizers, or insufflators.

When administered in the form of an aqueous liquid solution, the formulation will contain the glycopyrrolate active agent and purified water. Optional components in liquid solution include suitable solvents, buffering agents, sweeteners, anti-microbial preservatives, flavoring agents, and mixtures thereof. A component of the formulation may serve more than one function. For example, a suitable buffering agent may also act as a flavoring agent as well as a sweetener.

Suitable solvents in the liquid solution used in the present invention include, for example, sorbital, glycerin, propylene glycol, and water. A mixture of two or more solvents may optionally be used. The solvent or solvent system is typically present in an amount of from about 1% to about 90% by weight of the total liquid formulation.

Suitable buffering agents include, for example, citric acid, sodium citrate, phosphoric acid, potassium phosphate, and various other acids and salts. A mixture of two or more buffering agents may optionally be used. The buffering agent or mixtures thereof are typically present in an amount of from about 0.001 wt. % to about 4 wt. %.

Suitable sweeteners include, for example, saccharin sodium, sucrose, and mannitol. A mixture of two or more sweeteners may optionally be used. The sweetener or mixtures thereof are typically present in an amount of from about 0.001 wt. % to about 70 wt. %.

Suitable anti-microbial preservatives include, for example, methylparaben, propylparaben, sodium benzoate, benzalkoniyum chloride. A mixture of two or more preservatives may optionally be used. The preservative or mixtures thereof are typically present in an amount of from about 0.0001 wt. % to about 2 wt. %.

Suitable flavoring agents may be used to the liquid solution a cherry flavor, cotton candy flavor, or other suitable flavor to make the solution easier for a patient to ingest. The flavoring agent or mixtures thereof are typically present in an amount of from about 0.0001 wt. % to about 5 wt. %.

The following examples further illustrate the invention but, of course, should not be construed as in any way limiting its scope.

EXAMPLE 1

A preferred liquid formulation suitable for use in the method of the present invention contains the following components:

| Ingredient | Quantity (wt. %) |
| --- | --- |
| glycopyrrolate USP | 0.02 |
| sorbitol solution | 60.0 |
| glycerin | 10.0 |
| citric acid | 0.128 |
| sodium citrate | 0.064 |
| saccharin sodium | 0.05 |
| propylene glycol | 10.0 |
| methylparaben | 0.18 |
| propylparaben | 0.02 |
| cherry flavor | 0.10 |
| purified water | 19.438 |

Another aspect of the invention is a kit comprising a pharmaceutical composition comprising a therapeutically effective amount of glycopyrrolate and a pharmaceutically acceptable carrier, prescribing information, and a container.

The prescribing information is generally a piece of paper that includes instructions regarding the proper administration of glycopyrrolate. In the kit of the present invention, the prescribing information will include advice regarding the administration of glycopyrrolate without food to improve bioavailability. The prescribing information will be consistent with the methods of treatment described herein.

Such advice may be provided on the prescribing information in the form of a discussion of the increased bioavailability of glycopyrrolate if taken on an empty stomach as compared with its use if taken with food. The advice may optionally include pharmacokinetic data comparing the administration of glycopyrrolate taken under fasted and fed conditions. The advice may alternatively be provided in the form of instructions to take glycopyrrolate under fasted conditions. Such instructions may be provided in writing with the prescribing information alone or in combination with a discussion of the relative bioavailability of glycopyrrolate administered without and with food.

The pharmaceutical composition will be contained in any suitable container capable of holding and dispensing the dosage form and which will not significantly interact with the composition and will further be in physical relation with the prescribing information containing advice regarding the preferred administration of glycopyrrolate under fasted conditions. The container may be, for example, a cardboard box or plastic vial. Alternatively, the glycopyrrolate composition may be provided in individual unit dosage forms, such as plastic strips sealed with aluminum foil. Such unit dosage forms may optionally be further packaged in a box, vial, or other suitable container along with the prescribing information. When glycopyrrolate is to be administered with a second active agent, the two pharmaceutical dosage forms may be placed in the same or separate containers.

The prescribing information may be associated with the container by any means that maintain a physical proximity of the two. For example, they may both be contained in a packaging material such as a box or plastic shrink wrap. Alternatively, the prescribing information may be bonded to the container such as with suitable glue or other bonding or holding means such that the prescribing information is not obscured.

EXAMPLE 2

The effect of food on glycopyrrolate absorption in human patients was identified in a study designed to compare the bioavailability of 2 mg of glycopyrrolate in a liquid formulation administered to healthy volunteers with and without food. An object of the study was to evaluate the relative bioavailability of glycopyrrolate when administered to human subjects with and without food.

An open-label, randomized, crossover trial in healthy subjects was conducted over a 16-day treatment period which includes three (3) dosing periods. There was a one week washout period between each dose.

The two study drug treatments were as follows:

Treatment A—glycopyrrolate liquid 2 mg (10 mL dose of 1 mg per 5 mL solution) administered without food; and Treatment B—glycopyrrolate liquid 2 mg (10 mL dose of 1 mg per 5 mL solution) administered with food.

A single center, single dose, open label, two-period crossover trial was devised for study in healthy subjects. A total of 39 subjects (25 males and 14 females) were enrolled and dosed. Each administration was a single oral dose of 2 mg of glycopyrrolate liquid either without food (Group A) or with food (Group B). The plasma of subjects in the study were assayed and used for pharmacokinetic analysis.

The study drug was administered according to Treatment A (without food) and Treatment B (with food) as follows.

Treatment A—Without Food 10 mL of liquid containing 2 mg of glycopyrrolate (1 mg/5 mL) in the liquid formulation described in Example 1 was administered by an oral syringe. The glycopyrrolate liquid formulation was administered with 180 mL (6 fluid ounces) of water.

Subjects will have fasted from about 10 p.m. the day before dosing. Dosing occurred at about 8:00 a.m. Fasting continued for four (4) hours after the dosing. Water was allowed to be taken ad libitum from 2 hours after dosing.

Blood samples for pharmacokinetic analysis were taken immediately prior to dosing and at the following times after dosing: 0.25, 0.5, 1, 1.5, 2, 2.5, 3, 4, 6, 8, 12, 16, and 24 hours.

Treatment B—With Food 10 mL of liquid containing 2 mg of glycopyrrolate (1 mg/5 mL) in the liquid formulation described in Example 1 was administered by an oral syringe. The glycopyrrolate liquid formulation was administered with 180 mL (6 fluid ounces) of water. Breakfast was given to the subjects in Group A 30 minutes prior to dosing and eaten within a 30 minute period. The dose of glycopyrrolate was administered to the subjects immediately (i.e., within 5 minutes) after completion of breakfast.

Subjects will have fasted from about 10 p.m. the day before dosing. A high fat, high calorie breakfast was eaten at about 7:30 a.m. Dosing occurred immediately following completion of the meal at about 8:00 a.m. The dose was administered at the same time for an individual subject. No further food was permitted until lunch which did not occur until at least four (4) hours post dose. Water was allowed to be taken ad libitum from 2 hours after dosing.

The breakfast consisted of the following:

2 eggs (with one tablespoon butter for cooking eggs);

2 strips of bacon;

2 slices of toast with butter (with one tablespoon butter);

4 ounces of hash brown potatoes; and 1 glass whole milk (8 fluid ounces).

Blood samples for pharmacokinetic analysis were taken immediately prior to dosing and at the following times after dosing: 0.25, 0.5, 1, 1.5, 2, 2.5, 3, 4, 6, 8, 12, 16, and 24 hours.

All pharmacokinetic parameters were analyzed by non-compartmental methods. The following PK parameters were calculated for the two PK profiles and are defined as follows:

| | |
|---|---|
| $T_{max}$ | Time to maximum concentration; |
| $C_{max}$ | Observed maximum concentration; |
| $k_{el}$ | Slope of terminal linear portion of concentration/time curve; |
| $t_{1/2}$ | Apparent elimination half-life; |
| $AUC_{0-t}$ | Area under the curve to the concentration at time t as measured by the trapezoidal rule; |
| $AUC_{0-24\ hrs}$ | Area under the curve to the concentration at time t = 24 hours; and |
| $AUC_{0-\infty}$ | The AUC value extrapolated to infinity calculated as $AUC_{0-\infty} = AUC_{0-24\ hrs} + C_{24\ hrs}/k_{el}$ where $C_{24\ hrs}$ is the concentration measured at 24 hours after administration. |

Pharmacokinetic parameters were log-transformed by analysis and assessed using SAS® Least Square Means derived from a three-way analysis of variance (ANOVA) fitting effects for subject, treatment, and period. Treatments comparisons were made by calculating the difference and 95% confidence intervals (CIs) of the difference of the log SAS Least Square Means between parameters for the respective treatments. The differences and CIs about the differences were back-transformed for reporting purposes.

The individual test results for plasma glycopyrrolate parameters $AUC_{0-\infty}$ (ng*hr/mL), $AUC_{0-24}$ hrs (ng*hr/mL), $C_{max}$ (ng/mL), and $T_{max}$ (hr) are summarized in Tables I–IV, respectively. The pharmacokinetic parameters $k_{e1}$ and $t_{1/2}$ are estimated for descriptive purposes.

TABLE I

[0069] Comparison of $AUC_{0-\infty}$ (ng*hr/mL) and Ln $AUC_{0-\infty}$ Administered Without Food (Group A) v. Administered With Food (Group B)

| Subject Number | Group A fasted (ng/mL) | Group B fed (ng/mL) | Difference (A–B) | Ratio (A/B) | Ln Ratio (Ln A/B) |
|---|---|---|---|---|---|
| 001 | 3.3609 | 0.6642 | 2.6967 | 5.060 | 1.6214 |
| 002 | 0.6579 | 0.2815 | 0.3764 | 2.337 | 0.8489 |
| 003 | 1.5650 | 0.3288 | 1.2362 | 4.760 | 1.5602 |
| 004 | 4.5090 | 0.8646 | 3.6444 | 5.215 | 1.6516 |
| 005 | 0.6368 | 0.3438 | 0.2930 | 1.852 | 0.6164 |
| 006 | 1.7365 | 0.3274 | 1.4091 | 5.304 | 1.6684 |
| 007 | 0.6483 | 0.3568 | 0.2915 | 1.817 | 0.5972 |
| 008 | 1.5432 | 0.4953 | 1.0479 | 3.116 | 1.1364 |
| 009 | 2.4073 | 0.4374 | 1.9699 | 5.504 | 1.7054 |
| 010 | 0.8591 | 0.3496 | 0.5095 | 2.457 | 0.8991 |
| 011 | 0.8860 | 0.5555 | 0.3305 | 1.595 | 0.4668 |
| 012 | 1.2341 | 0.5596 | 0.6745 | 2.205 | 0.7909 |
| 013 | 3.2796 | 0.4734 | 2.8062 | 6.928 | 1.9355 |
| 014 | 2.9265 | 0.5345 | 2.3920 | 5.475 | 1.7002 |
| 015 | 0.7822 | 0.4643 | 0.3179 | 1.685 | 0.5216 |
| 016 | 1.7861 | 0.4619 | 1.3242 | 3.867 | 1.3524 |
| 017 | — | — | — | — | — |
| 018 | 1.1544 | 0.4513 | 0.7031 | 2.558 | 0.9392 |
| 019 | 1.5328 | 0.4736 | 1.0592 | 3.236 | 1.1745 |
| 020 | 1.1659 | 0.1557 | 1.0102 | 7.488 | 2.0133 |
| 021 | 1.7534 | 0.5257 | 1.2277 | 3.335 | 1.2046 |
| 022 | 2.3768 | — | — | — | — |
| 023 | 3.1990 | 0.3830 | 2.8160 | 8.352 | 2.1226 |
| 024 | 0.9916 | 0.4602 | 0.5314 | 2.155 | 0.7677 |
| 025 | 1.0543 | 0.3292 | 0.7251 | 3.203 | 1.1640 |
| 026 | 1.0993 | 0.5757 | 0.5236 | 1.910 | 0.6468 |
| 027 | 1.3869 | 0.3414 | 1.0455 | 4.062 | 1.4018 |
| 028 | 2.6432 | 0.4192 | 2.2240 | 6.305 | 1.8414 |
| 029 | — | — | — | — | — |
| 030 | 3.5489 | 0.6786 | 2.8703 | 5.230 | 1.6544 |
| 031 | 1.3621 | 0.3193 | 1.0428 | 4.266 | 1.4507 |
| 032 | 0.8257 | 0.4332 | 0.3925 | 1.906 | 0.6450 |
| 033 | 1.7290 | — | — | — | — |
| 034 | 4.7688 | 0.6349 | 4.1339 | 7.511 | 2.0164 |
| 035 | 0.8839 | 0.4115 | 0.4724 | 2.148 | 0.7645 |
| 036 | 1.2865 | 0.5715 | 0.7150 | 2.251 | 0.8114 |
| 117 | 2.2357 | 0.5499 | 1.6858 | 4.066 | 1.4026 |
| 129 | 2.4764 | 0.4979 | 1.9785 | 4.974 | 1.6042 |
| 133 | 0.6692 | 0.3633 | 0.3059 | 1.842 | 0.6109 |
| N | 37 | 35 | 35 | 35 | 35 |
| Mean | 1.8098 | 0.4592 | 1.3367 | 3.885 | 1.2374 |
| Std Dev | 1.0878 | 0.1347 | 1.0354 | 1.921 | 0.5001 |
| % CV | 60.1 | 29.3 | 77.5 | 49.4 | 40.4 |
| Median | 1.5328 | 0.4602 | 1.0455 | 3.335 | 1.2046 |
| Minimum | 0.6368 | 0.1557 | 0.2915 | 1.595 | 0.4668 |
| Maximum | 4.7688 | 0.8646 | 4.1339 | 8.352 | 2.1226 |

TABLE II

[0070] Comparison of $AUC_{0-24\ hrs}$ (ng*hr/mL) and Ln $AUC_{0-24\ hrs}$ Administered Without Food (Group A) v. Administered With Food (Group B)

| Subject Number | Group A fasted (ng/mL) | Group B fed (ng/mL) | Difference (A–B) | Ratio (A/B) | Ln Ratio (Ln A/B) |
|---|---|---|---|---|---|
| 001 | 3.2789 | 0.5337 | 2.7452 | 6.144 | 1.8154 |
| 002 | 0.6015 | 0.1302 | 0.4713 | 4.620 | 1.5304 |
| 003 | 1.5151 | 0.2746 | 1.2405 | 5.517 | 1.7079 |
| 004 | 4.3370 | 0.7616 | 3.5754 | 5.695 | 1.7395 |
| 005 | 0.6174 | 0.1394 | 0.4780 | 4.429 | 1.4882 |
| 006 | 1.7029 | 0.2800 | 1.4229 | 6.082 | 1.8053 |
| 007 | 0.5486 | 0.2865 | 0.2621 | 1.915 | 0.6496 |
| 008 | 1.5023 | 0.4603 | 1.0420 | 3.264 | 1.1829 |
| 009 | 2.3508 | 0.3516 | 1.9992 | 6.686 | 1.9000 |
| 010 | 0.8025 | 0.2762 | 0.5263 | 2.906 | 1.0666 |
| 011 | 0.7598 | 0.4083 | 0.3515 | 1.861 | 0.6211 |
| 012 | 1.1953 | 0.4710 | 0.7243 | 2.538 | 0.9313 |
| 013 | 3.2238 | 0.4053 | 2.8185 | 7.954 | 2.0737 |
| 014 | 2.8080 | 0.4643 | 2.3437 | 6.048 | 1.7997 |
| 015 | 0.6496 | 0.4193 | 0.2303 | 1.549 | 0.4378 |
| 016 | 1.7377 | 0.3861 | 1.3516 | 4.501 | 1.5042 |
| 017 | — | — | — | — | — |
| 018 | 1.0881 | 0.4005 | 0.6876 | 2.717 | 0.9995 |
| 019 | 1.4534 | 0.3041 | 1.1493 | 4.779 | 1.5643 |
| 020 | 1.0868 | 0.1155 | 0.9713 | 9.410 | 2.2417 |
| 021 | 1.6919 | 0.4643 | 1.2276 | 3.644 | 1.2931 |
| 022 | 2.3242 | 0.5343 | 1.7899 | 4.350 | 1.4702 |
| 023 | 3.0914 | 0.3348 | 2.7566 | 9.234 | 2.2228 |
| 024 | 0.9414 | 0.3213 | 0.6201 | 2.930 | 1.0750 |
| 025 | 1.0261 | 0.2838 | 0.7423 | 3.616 | 1.2853 |
| 026 | 1.0423 | 0.5235 | 0.5188 | 1.991 | 0.6886 |
| 027 | 1.3460 | 0.2810 | 1.0650 | 4.790 | 1.5665 |
| 028 | 2.5938 | 0.3625 | 2.2313 | 7.155 | 1.9679 |
| 029 | — | — | — | — | — |
| 030 | 3.4602 | 0.6097 | 2.8505 | 5.675 | 1.7361 |
| 031 | 1.3102 | 0.2389 | 1.0713 | 5.484 | 1.7019 |
| 032 | 0.7319 | 0.2873 | 0.4446 | 2.548 | 0.9351 |
| 033 | 1.6329 | — | — | — | — |
| 034 | 4.5894 | 0.5466 | 4.0428 | 8.396 | 2.1278 |
| 035 | 0.7945 | 0.3695 | 0.4250 | 2.150 | 0.7656 |
| 036 | 1.2253 | 0.4947 | 0.7306 | 2.477 | 0.9070 |
| 117 | 2.1502 | 0.5077 | 1.6425 | 4.235 | 1.4434 |
| 129 | 2.4003 | 0.4508 | 1.9495 | 5.325 | 1.6723 |
| 133 | 0.6238 | 0.3234 | 0.3004 | 1.929 | 0.6569 |
| N | 37 | 36 | 36 | 36 | 36 |
| Mean | 1.7361 | 0.3834 | 1.3556 | 4.571 | 1.4048 |

TABLE II-continued

[0070] Comparison of $AUC_{0-24\ hrs}$ (ng*hr/mL) and Ln $AUC_{0-24\ hrs}$ Administered Without Food (Group A) v. Administered With Food (Group B)

| Subject Number | Group A fasted (ng/mL) | Group B fed (ng/mL) | Difference (A–B) | Ratio (A/B) | Ln Ratio (Ln A/B) |
|---|---|---|---|---|---|
| Std Dev | 1.0693 | 0.1368 | 1.0008 | 2.154 | 0.4988 |
| % CV | 61.6 | 35.7 | 73.8 | 47.1 | 35.5 |
| Median | 1.4534 | 0.3778 | 1.0682 | 4.465 | 1.4962 |
| Minimum | 0.5486 | 0.1155 | 0.2303 | 1.549 | 0.4378 |
| Maximum | 4.5894 | 0.7616 | 4.0428 | 9.410 | 2.2417 |

TABLE III

[0071] Comparison of $C_{max}$ (ng/mL) and Ln $C_{max}$ Administered Without Food (Group A) v. Administered With Food (Group B)

| Subject Number | Group A fasted (ng/mL) | Group B fed (ng/mL) | Difference (A–B) | Ratio (A/B) | Ln Ratio (A/B) |
|---|---|---|---|---|---|
| 001 | 0.5210 | 0.0951 | 0.4259 | 5.478 | 1.7008 |
| 002 | 0.0975 | 0.0287 | 0.0688 | 3.397 | 1.2230 |
| 003 | 0.3780 | 0.0567 | 0.3213 | 6.667 | 1.8971 |
| 004 | 0.8350 | 0.5430 | 0.2920 | 1.538 | 0.4303 |
| 005 | 0.1560 | 0.0301 | 0.1259 | 5.183 | 1.6453 |
| 006 | 0.2920 | 0.0540 | 0.2380 | 5.407 | 1.6878 |
| 007 | 0.1220 | 0.1120 | 0.0100 | 1.089 | 0.0855 |
| 008 | 0.2030 | 0.0575 | 0.1455 | 3.530 | 1.2614 |
| 009 | 0.5800 | 0.0735 | 0.5065 | 7.891 | 2.0657 |
| 010 | 0.1630 | 0.0574 | 0.1056 | 2.840 | 1.0437 |
| 011 | 0.1560 | 0.0748 | 0.0812 | 2.086 | 0.7350 |
| 012 | 0.2540 | 0.0871 | 0.1669 | 2.916 | 1.0703 |
| 013 | 0.4470 | 0.0832 | 0.3638 | 5.373 | 1.6813 |
| 014 | 0.3820 | 0.0583 | 0.3237 | 6.552 | 1.8798 |
| 015 | 0.0697 | 0.0625 | 0.0072 | 1.115 | 0.1090 |
| 016 | 0.3050 | 0.0845 | 0.2205 | 3.609 | 1.2836 |
| 017 | — | — | — | — | — |
| 018 | 0.2340 | 0.1090 | 0.1250 | 2.147 | 0.7640 |
| 019 | 0.1940 | 0.0570 | 0.1370 | 3.404 | 1.2248 |
| 020 | 0.2650 | 0.0386 | 0.2264 | 6.865 | 1.9265 |
| 021 | 0.2750 | 0.0551 | 0.2199 | 4.991 | 1.6076 |
| 022 | 0.3730 | 0.0684 | 0.3046 | 5.453 | 1.6962 |
| 023 | 0.8340 | 0.0765 | 0.7575 | 10.902 | 2.3889 |
| 024 | 0.2150 | 0.0573 | 0.1577 | 3.752 | 1.3223 |
| 025 | 0.1920 | 0.0669 | 0.1251 | 2.870 | 1.0543 |
| 026 | 0.2140 | 0.0891 | 0.1249 | 2.402 | 0.8762 |
| 027 | 0.1950 | 0.0556 | 0.1394 | 3.507 | 1.2548 |
| 028 | 0.6680 | 0.0822 | 0.5858 | 8.127 | 2.0951 |
| 029 | — | — | — | — | — |
| 030 | 0.5450 | 0.1010 | 0.4440 | 5.396 | 1.6857 |
| 031 | 0.2350 | 0.0494 | 0.1856 | 4.757 | 1.5596 |
| 032 | 0.1550 | 0.0599 | 0.0951 | 2.588 | 0.9507 |
| 033 | 0.2620 | — | — | — | — |
| 034 | 0.5670 | 0.0799 | 0.4871 | 7.096 | 1.9596 |
| 035 | 0.2020 | 0.0983 | 0.1037 | 2.055 | 0.7202 |
| 036 | 0.2740 | 0.0937 | 0.1803 | 2.924 | 1.0730 |
| 117 | 0.3680 | 0.0789 | 0.2891 | 4.664 | 1.5399 |
| 129 | 0.3010 | 0.0670 | 0.2340 | 4.493 | 1.5024 |
| 133 | 0.2280 | 0.0730 | 0.1550 | 3.123 | 1.1389 |
| N | 37 | 36 | 36 | 36 | 36 |
| Mean | 0.3178 | 0.0838 | 0.2356 | 4.339 | 1.3372 |
| Std Dev | 0.1895 | 0.0813 | 0.1658 | 2.180 | 0.5394 |
| % CV | 59.6 | 97.0 | 70.4 | 50.2 | 40.3 |
| Median | 0.2620 | 0.0707 | 0.1830 | 3.681 | 1.3029 |
| Minimum | 0.0697 | 0.0287 | 0.0072 | 1.089 | 0.0855 |
| Maximum | 0.8350 | 0.5430 | 0.7575 | 10.902 | 2.3889 |

TABLE IV

[0072] Comparison of $T_{max}$ (hr) Administered Without Food (Group A) v. Administered With Food (Group B)

| Subject Number | Group A fasted (hr) | Group B fed (hr) | Difference (A–B) | Ratio (A/B) |
|---|---|---|---|---|
| 001 | 4.000 | 2.000 | 2.000 | 2.000 |
| 002 | 2.500 | 1.500 | 1.000 | 1.667 |
| 003 | 2.500 | 2.000 | 0.500 | 1.250 |
| 004 | 2.500 | 2.500 | 0.000 | 1.000 |
| 005 | 3.000 | 2.020 | 0.980 | 1.485 |
| 006 | 6.000 | 2.000 | 4.000 | 3.000 |
| 007 | 2.500 | 2.500 | 0.000 | 1.000 |
| 008 | 4.000 | 6.080 | -2.080 | 0.658 |
| 009 | 2.500 | 2.500 | 0.000 | 1.000 |
| 010 | 2.500 | 2.000 | 0.500 | 1.250 |
| 011 | 0.500 | 3.000 | -2.500 | 0.167 |
| 012 | 3.000 | 3.000 | 0.000 | 1.000 |
| 013 | 4.000 | 2.500 | 1.500 | 1.600 |
| 014 | 4.000 | 2.500 | 1.500 | 1.600 |
| 015 | 4.000 | 4.000 | 0.000 | 1.000 |
| 016 | 2.500 | 2.500 | 0.000 | 1.000 |
| 017 | — | — | — | — |
| 018 | 2.500 | 2.000 | 0.500 | 1.250 |
| 019 | 2.500 | 2.500 | 0.000 | 1.000 |
| 020 | 2.520 | 1.500 | 1.020 | 1.680 |
| 021 | 3.000 | 6.000 | -3.000 | 0.500 |
| 022 | 4.000 | 2.500 | 1.500 | 1.600 |
| 023 | 4.000 | 2.000 | 2.000 | 2.000 |
| 024 | 2.620 | 2.000 | 0.620 | 1.310 |
| 025 | 4.000 | 1.500 | 2.500 | 2.667 |
| 026 | 2.530 | 2.000 | 0.530 | 1.265 |
| 027 | 2.530 | 3.000 | -0.470 | 0.843 |
| 028 | 2.500 | 2.500 | 0.000 | 1.000 |
| 029 | — | — | — | — |
| 030 | 4.000 | 2.000 | 2.000 | 2.000 |
| 031 | 4.000 | 1.000 | 3.000 | 4.000 |
| 032 | 2.000 | 1.500 | 0.500 | 1.333 |
| 033 | 3.000 | — | — | — |
| 034 | 6.000 | 4.000 | 2.000 | 1.500 |
| 035 | 2.500 | 2.000 | 0.500 | 1.250 |
| 036 | 2.500 | 4.000 | -1.500 | 0.625 |
| 117 | 4.000 | 3.000 | 1.000 | 1.333 |
| 129 | 2.000 | 4.000 | -2.000 | 0.500 |
| 133 | 2.030 | 2.000 | 0.030 | 1.015 |
| N | 37 | 36 | 36 | 36 |
| Mean | 3.101 | 2.600 | 0.504 | 1.371 |
| Std Dev | 1.075 | 1.120 | 1.482 | 0.725 |
| % CV | 34.7 | 43.1 | 294.2 | 52.9 |
| Median | 2.530 | 2.500 | 0.500 | 1.250 |
| Minimum | 0.500 | 1.000 | -3.000 | 0.167 |
| Maximum | 6.000 | 6.080 | 4.000 | 4.000 |

Figure 2:
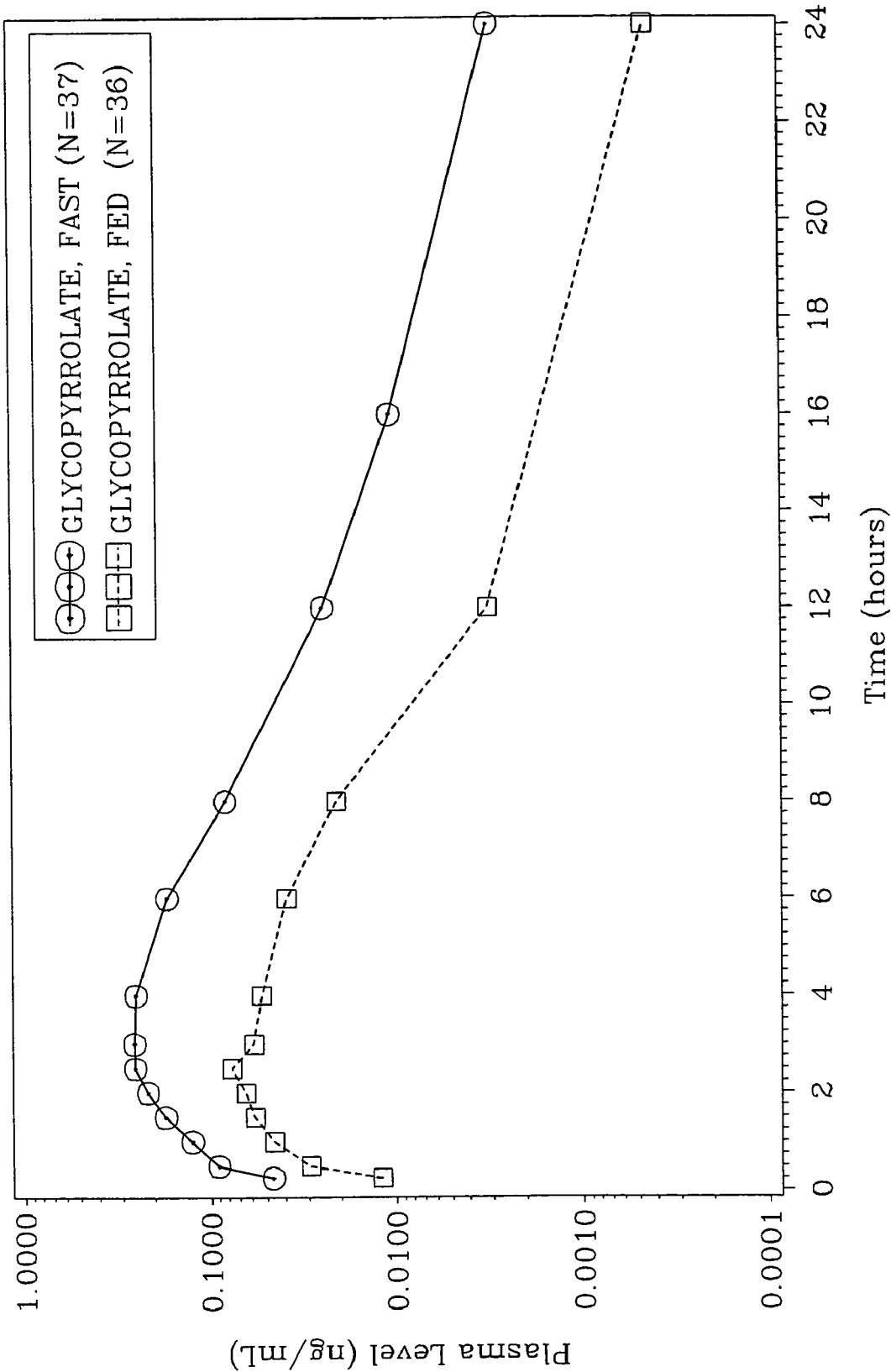
FIG. 2 is a plot of the mean plasma concentration of glycopyrrolate in nanograms per milliliter (semi-log) versus the time elapsed from administration of a liquid glycopyrrolate dosage form (2 mg dose of 1 mg/5 mL liquid solution). Two plots are shown for the liquid glycopyrrolate dosage form administered under fasted and fed conditions.

The results of the pharmacokinetic analysis of the subjects' mean plasma glycopyrrolate concentration over time administered under fasted and fed conditions are set forth in FIGS. 1 and 2. FIG. 1 is a plot of the mean concentration (ng/mL) and FIG. 2 is a plot of a semi-log of the mean concentration (ng/mL). As the figures illustrate, the Cmax and AUC are significantly greater for glycopyrrolate administered without food.

Based on arithmetic means, the mean $AUC_{0-24\ hrs}$ for glycopyrrolate administered under fasted conditions was 1.7361±1.069 ng*hr/mL and for glycopyrrolate administered under fed conditions was 0.3834±0.1368 ng*hr/mL. Thus, the mean $AUC_{0-24\ hrs}$ for Group A (fasted) was more than 4.5 times higher than the mean $AUC_{0-24\ hrs}$ for Group B (fed).

The results for AUC extrapolated to infinity were similar. The mean $AUC_{0-\infty}$ for glycopyrrolate administered under fasted conditions was 1.8098±1.0878 ng*hr/mL. For glycopyrrolate administered under fed conditions, the mean $AUC_{0-\infty}$ was 0.3834 ng*hr/mL±0.1368. The mean $AUC_{0-}$ ∞ for Group A sted) was more than 4.7 times higher than the mean $AUC_{0-\infty}$ for Group B (fed).

The mean maximum plasma concentration $C_{max}$ of glycopyrrolate was 0.3178±0.1895 ng/mL for subjects in Group A (administration without food) and 0.0838±0.0813 ng/mL for subjects in group B (administration with food). The mean $C_{max}$ for Group A (fasted) was about 3.8 times greater than the mean $C_{max}$ for Group B (fed).

The food effect on the pharmacokinetic parameters of glycopyrrolate following the administration of 2 mg of the liquid glycopyrrolate formulation (10 mL of 1 mg/5 mL liquid solution) was appreciable.

Table V summarizes the results of the analyses performed on the pharmacokinetic parameters obtained from the fasted and fed states. LS is an abbreviation for least squared.

TABLE V

[0079] Plasma Glycopyrrolate Pharmacokinetic Parameters - Without Food (Group A) v. With Food (Group B)

| Parameter | LS Mean Group A fasted (N subjects) | LS Mean Group B fed (N subjects) | Ratio (A–B) | 95% Confidence Interval |
|---|---|---|---|---|
| Ln $AUC_{0-24\ hrs}$ | 0.41704(37) | −0.98781(36) | 4.075 | [3.4102; 4.8692] |
| Ln $AUC_{0-\infty}$ | 0.47407(37) | −0.76683(35) | 3.459 | [2.9175; 4.1003] |
| Ln $C_{max}$ | −1.26674(37) | −2.60398(36) | 3.809 | [3.1392; 4.6205] |
| $AUC_{0-24\ hrs}$ (ng*hr/mL) | 1.84116(37) | 0.48561(36) | 3.791 | [3.1347; 4.4482] |
| $AUC_{0-\infty}$ (ng*hr/mL) | 1.93908(37) | 0.60265(35) | 3.218 | [2.6754; 3.7598] |
| $C_{max}$ (ng/mL) | 0.33727(37) | 0.10171(36) | 3.316 | [2.7462; 3.8855] |
| $T_{max}$ (hr) | 3.15163(37) | 2.64802(36) | 1.190 | [1.0126; 1.3678] |
| $k_{el}$ (1/hr) | 0.26358(37) | 0.22831(35) | 1.154 | [0.9906; 1.3183] |
| $t_{½}$ (hr) | 2.98144(37) | 3.25297(35) | 0.917 | [0.7416; 1.0915] |

With a 5% significance level, the ANOVA detected statistically significant differences between glycopyrrolate fasted and fed conditions for Ln-transformed $AUC_{0-24\ hrs}$, $AUC_{0-\infty}$, and $C_{max}$ as well as for untransformed $AUC_{0-24\ hrs}$, $AUC_{0-\infty}$, and $C_{max}$.

The ratio (A/B) of least-square means for $AUC_{0-24\ hrs}$, $AUC_{0-\infty}$, and $C_{max}$ were 379.1%, 321.8%, and 331.6%, respectively, demonstrating that glycopyrrolate administered without food increased the extent of absorption.

In sum, the administration of glycopyrrolate without food increases the extent of absorption of a glycopyrrolate liquid solution when administered as a single 2 mg dose (10 mL of 1 mg/5 mL liquid solution). The bioavailability of a glycopyrrolate liquid solution increased when administered without food as compared to the administration of glycopyrrolate with food.

For any suitable pharmaceutical dosage form containing a therapeutically effective amount of glycopyrrolate, the $C_{max}$ following administration under fasted conditions is typically at least about 2.5 ng/mL, and preferably at least about 3.0 ng/mL. The ratio of $C_{max}$ for glycopyrrolate (in any dosage form) administered without food to $C_{max}$ following administration with food is generally greater than about 1.1, preferably greater than about 2.8, and more preferably greater than about 3.8.

The $AUC_{0-24\ hrs}$ and $AUC_{0-\infty}$ for glycopyrrolate (in any pharmaceutical dosage form) are typically greater than about 0.8 ng*hr/mL following administration without food, preferably at least about 1.0 ng*/hr/mL, and more preferably at least about 1.7 ng*hr/mL. The ratio of $AUC_{0-24\ hrs}$ and $AUC_{0-\infty}$ for glycopyrrolate (in any dosage form) administered without food to $AUC_{0-24\ hrs}$ and $AUC_{0\infty}$ following administration with food is generally greater than about 1.8, preferably greater than about 4.5, and more preferably greater than about 5.5.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of increasing the oral bioavailability of glycopyrrolate to a patient receiving glycopyrrolate therapy comprising administering to the patient a pharmaceutical tablet comprising about 1 mg to about 10 mg of glycopyrrolate under fasted conditions, wherein the administration results in an increase of the maximum plasma concentration ($C_{max}$) and the extent of absorption of glycopyrrolate at t=24 hours ($AUC_{0-24hrs}$) as compared to the administration of glycopyrrolate under fed conditions.

2. The method of claim 1 wherein the ratio of $C_{max}$ following administration without food to $C_{max}$ following administration with food is greater than about 1.1, and wherein the ratio of $AUC_{0-24\ hrs}$ following administration without food to $AUC_{0-24\ hrs}$ following administration with food is greater than about 1.8.

3. The method of claim 2 wherein the ratio of $C_{max}$ following administration without food to $C_{max}$ following administration with food is greater than about 2.8, and wherein the ratio of $AUC_{0\text{-}24\ hrs}$ following administration without food to $AUC_{0\text{-}24\ hrs}$ following administration with food is greater than about 4.5.

4. The method of claim 2, further comprising informing the patient that the administration of the glycopyrrolate dose in a pharmaceutical composition under fasted conditions results in an increase of the maximum plasma concentration ($C_{max}$) and of the extent of absorption of glycopyrrolate at t=24 hours ($AUC_{0\text{-}24\ hrs}$) as compared to the administration of glycopyrrolate under fed conditions.

5. The method of claim 4, wherein the pharmaceutical composition is provided to a patient in a container associated with prescribing information that advises the patient that the administration of the glycopyrrolate dose in a pharmaceutical composition under fasted conditions results in an increase of the maximum plasma concentration ($C_{max}$) and of the extent of absorption of glycopyrrolate at t=24 hours ($AUC_{0\text{-}24\ hrs}$) as compared to the administration of glycopyrrolate under fed conditions.

* * * * *